US005560850A

United States Patent [19]

Hoppe et al.

[11] Patent Number: 5,560,850
[45] Date of Patent: Oct. 1, 1996

[54] BIODEGRADABLE OLIGOESTERS SUITABLE AS LUBRICANTS

[75] Inventors: Dirk Hoppe, Nottuln; Clemens Auschra, Mainz, both of Germany

[73] Assignee: Roehm GmbH Chemische Fabrik, Darmstadt, Germany

[21] Appl. No.: 542,931

[22] Filed: Oct. 13, 1995

[30] Foreign Application Priority Data

Oct. 15, 1994 [DE] Germany ............................ 44 37 007.5

[51] Int. Cl.$^6$ ................................................ C10M 105/36
[52] U.S. Cl. ............................ 508/485; 528/272; 560/194
[58] Field of Search .................................. 252/56 R, 56 S; 528/272

[56] References Cited

U.S. PATENT DOCUMENTS

| | | |
|---|---|---|
| 2,817,673 | 12/1957 | Roelen et al. |
| 5,358,650 | 10/1994 | Srinivasan et al. ............... 252/56 R |
| 5,378,249 | 1/1995 | Morrison ........................... 252/56 R |
| 5,382,374 | 1/1995 | Takemitsu et al. ................ 252/56 S |
| 5,434,237 | 7/1995 | Weinelt et al. .................... 528/272 |

OTHER PUBLICATIONS

Kirk–Othmer, "Thyroid and Antithyroid Preparations to Vinyl Polymers", Encyclopedia of Chemical Technology, vol. 23, 3rd Ed., pp. 224–226. Date Unavailable.
Kirk–Othmer, "Elastomers, Polyisoprene to Expert Systems", Encyclopedia of Chemical Technology, vol. 9, 4th Ed., pp. 755–812. Date Unavailable.

*Primary Examiner*—Jacqueline V. Howard
*Attorney, Agent, or Firm*—Oblon, Spivak, McClelland, Maier & Neustadt, P.C.

[57] ABSTRACT

New oligoesters made from a tricyclic diol with 8 to 20 carbon atoms, a dicarboxylic acid with 4 to 20 carbon atoms, and an aliphatic alcohol with 1 to 30 carbon atoms are useful as lubricants, hydraulic oils and compressor oils for mobile field use in forestry and agriculture, in construction, in mining and in transport. The oligoesters have a kinematic viscosity of 50 to 50,000 mm$^2$/s at 40° C. and are biodegradable.

8 Claims, No Drawings

BIODEGRADABLE OLIGOESTERS SUITABLE AS LUBRICANTS

BACKGROUND OF THE INVENTION

1. Field of the Invention

The invention relates to biodegradable oligoesters suitable as lubricants, made from a tricyclic diol with 8 to 20 carbon atoms, a saturated, straight-chain or branched dicarboxylic acid with 4 to 20 carbon atoms, and an aliphatic alcohol with 1 to 30 carbon atoms, as well as the use of these oligoesters as lubricants. The oligoesters according to the invention have a kinematic viscosity of 50 to 50,000 mm$^2$/s at 40° C.

2. Discussion of the Background

Synthetic esters, such as aliphatic and aromatic dicarboxylic acid diesters, dimeric acid esters and pentaerythritol tetraesters, for example, as well as natural esters such as canola oil, are used in lubricant technology in many different areas. They are characterized by good lubricant properties and have a high viscosity index, unless they are aromatic esters, and are generally easily biodegradable, in contrast to products based on mineral oil and other hydrocarbons, such as poly(alpha-olefins).

Until now, ester oils with high viscosity that have a low solidification point, are biodegradable and demonstrate good lubricant properties have not been available. The canola oils and dimeric acid esters which have a relatively high viscosity tend to gum up, because of the double bond which is still present, and are very sensitive to oxidation, so that there are many purposes for which they cannot be used.

SUMMARY OF THE INVENTION

It is, therefore, an object of the present invention to provide ester oils with high viscosity which demonstrate good biodegradability and good lubricant properties.

It has now, surprisingly, been found that oligoesters of a tricyclic diol, an aliphatic dicarboxylic acid and an aliphatic alcohol as the end group meet the above requirements.

DETAILED DESCRIPTION OF THE PREFERRED EMBODIMENTS

The oligoesters of the invention have a kinematic viscosity of about 50 to 50,000 mm$^2$/s at 40° C., and are produced from a saturated tricyclic diol with 8 to 20, preferably 10–20 carbon atoms; a saturated, straight-chain or branched dicarboxylic acid with 4 to 20 carbon atoms; and an aliphatic alcohol with 1 to 30 carbon atoms. The preferred tricyclic diol is an isomer mixture of dihydroxymethyl-(5.2.1.0$^{(2,6)}$) tricyclodecane, which is referred to below by its trade name of DICIDOL.

The aliphatic dicarboxylic acids are saturated, straight-chain or branched dicarboxylic acids with 4 to 20 carbon atoms. Dicarboxylic acids with 6 to 18 carbon atoms are preferred, straight-chain dicarboxylic acids with 6 to 18 carbon atoms are especially preferred.

The aliphatic alcohol is a straight-chain or branched mono-alcohol with 1 to 30 carbon atoms. Alcohols with 2 to 20 carbon atoms are preferred.

Preferably, the molar ratio of the dicarboxylic acid to the tricyclic diol is from 1:0.3 to 0.5:1. Preferably, the molar content of the aliphatic alcohol in the oligoesters of the invention will be between 0 and 1.4 relative to 1 mol of dicarboxylic acid.

The oligoesters according to the invention can be used alone (100 wt. %) or in mixtures with conventional base oils, for example dicarboxylic acid esters, mineral oils and poly(alphaolefins), as well as with suitable additives for formulating a broad range of lubricants. The oligoesters according to the invention are particularly suitable for the production of biodegradable lubricants with high viscosity, such as biodegradable hydraulic oils and compressor oils for mobile field use in forestry and agriculture, in construction, and in mining as well as in transport. For example, the oligoester of the invention or a lubricant composition containing the oligoester can be used to lubricate machine parts by applying the lubricant to the machine parts in a conventional manner.

The amount of oligoester of the present invention contained in mixtures with a base oil is not critical so long as the desired degree of lubrication and the desired viscosity and biodegradability properties are obtained. Generally, however, the oligoester will be present in an amount of about 1–90 wt %, preferably about 10–70 wt. % of the total oil composition.

The oligoesters of the present invention can be prepared by conventional esterification and transesterification reactions which are well-known in this art. Suitable esterification and transesterification reaction procedures are described, for example, in the Encyclopedia of Chemical Technology, Fourth Edition, Volume 9, pages 755–812 and the literature references cited therein. A particularly preferred method for preparing the oligoesters of the present invention is an ester-alcohol interchange reaction in which the tricyclic diol is reacted with an ester of the aliphatic dicarboxylic acid and the aliphatic alcohol. Ester-alcohol interchange reactions are well-known in the art and described in the Encyclopedia of Chemical Technology citation noted above. Typically, these interchange reactions are conducted in the presence of a catalyst, for example, alkaline catalysts such as alkali metal alkoxides, organic titanates, divalent metal salts such as zinc or manganese acetate, and organo-tin compounds such as dibutyl tin oxide. Acid catalysts such as sulfuric acid, sulfonic acids and hydrochloric acid may also be used. Neutral organic titanate catalysts, for example compounds having the structure MgTi(OR)$_6$ and (OR)$_4$Ti, are particularly preferred and are described, for example, in the Encyclopedia of Chemical Technology, Third Edition, Volume 23, pages 224–226 and the references cited therein. In these catalysts, R is preferably C$_{1-10}$ alkyl.

Other features of the invention will become apparent in the course of the following descriptions of exemplary embodiments which are given for illustration of the invention but are not intended to be limiting thereof.

EXAMPLES

Example 1

426 parts bis(2-ethylhexyl)sebacate and 98 parts DICIDOL were heated to 160° C. in a three-neck flask, while stirring and flushing with nitrogen. At this temperature, 1 part tetrabutyl titanate was added. Subsequently, the temperature was raised to 180° C. and the 2-ethyl hexanol which forms was first distilled off at a pressure of 300 mbar. The pressure was then reduced to 0.2 mbar in order to remove the alcohol completely. After cooling to 100° C., 20 parts water were added, and after stirring at this temperature for one hour, the titanium oxide hydrate was removed by filtration. The yield was almost quantitative. The product had the following properties: (KV: kinematic viscosity)

| KV (40° C.) | 146.2 mm²/s | DIN 51 562 |
| KV (100° C.) | 20.3 mm²/s | DIN 51 562 |
| Viscosity index | 161.1 | DIN ISO 2909 |
| Pour Point | −45° C. | DIN ISO 3016 |
| FZG* load level | 6% | DIN 51 354 |
| Biodegradability | 88% | CEC-L-33-T-82 |

*FZG: Research Institute for Gearwheels and Transmissions

Example 2

426 parts bis(2-ethylhexyl)sebacate and 108 parts DICIDOL were heated to 160° C. in a three-neck flask, while stirring and flushing with nitrogen. At this temperature, 1 part tetrabutyl titanate was added. Subsequently, the temperature was raised to 190° C. and the 2-ethyl hexanol which forms was first distilled off at a pressure of 300 mbar. The pressure was then reduced to 0.2 mbar, in order to remove the alcohol completely. After cooling to 100° C., 20 parts water were added, and after stirring at this temperature for one hour, the titanium oxide hydrate was removed by filtration. The yield was almost quantitative. The product had the following properties: (KV: kinematic viscosity)

| KV (40° C.) | 228.3 mm²/s | DIN 51 562 |
| KV (100° C.) | 27.9 mm²/s | DIN 51 562 |
| Viscosity index | 159.0 | DIN ISO 2909 |
| Pour Point | −45° C. | DIN ISO 3016 |
| FZG load level | 6% | DIN 51 354 |
| Biodegradability | 91% | CEC-L-33-T-82 |

Example 3

426 parts bis(2-ethylhexyl)sebacate and 138 parts DICIDOL were heated to 160° C. in a three-neck flask, while stirring and flushing with nitrogen. At this temperature, 1 part tetrabutyl titanate was added. Subsequently, the temperature was raised to 0.2 mbar, in order to remove the alcohol completely. After cooling to 100° C., 20 parts water were added, and after stirring at this temperature for one hour, the titanium oxide hydrate was removed by filtration. The yield was almost quantitative. The product had the following properties: (KV: kinematic viscosity)

| KV (40° C.) | 966.3 mm²/s | DIN 51 562 |
| KV (100° C.) | 81.5 mm²/s | DIN 51 562 |
| Viscosity index | 164.0 | DIN ISO 2909 |
| Pour Point | −45° C. | DIN ISO 3016 |
| FZG load level | 5% | DIN 51 354 |
| Biodegradability | 80% | CEC-L-33-T-82 |

Example 4

426 parts bis(2-ethylhexyl)sebacate and 108 parts DICIDOL were heated to 160° C. in a three-neck flask, while stirring and flushing with nitrogen. At this temperature, 1 part tetrabutyl titanate was added. Subsequently, the temperature was raised to 190° C. and the 2-ethyl hexanol which forms was first distilled off at a pressure of 300 mbar. The pressure was then reduced to 0.2 mbar, in order to remove the alcohol completely. After cooling to 100° C., 20 parts water were added, and after stirring at this temperature for one hour, the titanium oxide hydrate was removed by filtration. The yield was almost quantitative. The product had the following properties: (KV: kinematic viscosity)

| KV (40° C.) | 245.2 mm²/s | DIN 51 562 |
| KV (100° C.) | 28.3 mm²/s | DIN 51 562 |
| Viscosity index | 164.0 | DIN IS 2909 |
| Pour Point | −45° C. | DIN ISO 3016 |
| FZG load level | 6% | DIN 51 354 |
| Biodegradability | 92% | CEC-L-33-T-82 |

Obviously numerous modifications and variations of the present invention are possible in light of the above teachings. It is, therefore, to be understood that within the scope of the appended claims, the invention may be practiced otherwise than as specifically described therein.

Applicants incorporate herein by reference German Priority Application No. P 44 37 007.5, filed Oct. 15, 1994, in its entirety.

What is claimed as new and is desired to be secured by Letters Patent of the United States is:

1. An oligoester of a $C_{8-20}$ tricyclic diol, a saturated, straight-chain or branched $C_{4-20}$ dicarboxylic acid, and a $C_{1-30}$ aliphatic alcohol, said oligoester having a kinematic viscosity of about 50 to 50,000 mm²/s at 40° C.

2. The oligoester of claim 1, wherein said tricyclic diol is a dihydroxymethyl $(5,2,1,0^{(2,6)})$ tricyclodecane.

3. The oligoester of claim 1, wherein said dicarboxylic acid contains 6 to 18 carbon atoms.

4. The oligoester of claim 1, wherein said aliphatic alcohol contains 2 to 20 carbon atoms.

5. The oligoester of claim 1, wherein the molar ratio of said dicarboxylic to said tricyclic diol is from 1:0.3 to 0.5:1.

6. A lubricant composition, comprising a base oil and the oligoester of claim 1.

7. A method of lubricating machine parts, comprising contacting said machine parts with the oligoester of claim 1.

8. A method of lubricating machine parts, comprising contacting said machine parts with the lubricant composition of claim 6.

* * * * *